United States Patent [19]

Miser

[11] Patent Number: 4,919,132
[45] Date of Patent: Apr. 24, 1990

[54] APPARATUS FOR SUPPLYING GAS TO A PATIENT

[76] Inventor: Martin G. Miser, Star Rte. 3, Box 5498, Pagosa Springs, Colo. 81147

[21] Appl. No.: 366,233

[22] Filed: Jun. 12, 1989

Related U.S. Application Data

[63] Continuation of Ser. No. 88,128, Aug. 21, 1987, abandoned.

[51] Int. Cl.$^5$ ............................................. A61M 16/00
[52] U.S. Cl. ............................ 128/205.17; 128/205.24; 116/334; 116/277
[58] Field of Search ....................... 128/205.11, 205.13, 128/205.14, 205.17, 205.24, 205.23, 203.28, 203.29, 725; 116/277, 334, 307, 321, 266, 320, 335; 251/341, 344; 272/99

[56] References Cited

U.S. PATENT DOCUMENTS

| | | | |
|---|---|---|---|
| 2,944,546 | 7/1960 | Ziherl et al. | 128/ |
| 3,046,978 | 7/1962 | Lea | 128/205.13 |
| 3,850,171 | 11/1974 | Ball et al. | 128/205.11 |
| 3,913,607 | 10/1975 | Price | 137/ |
| 3,977,432 | 8/1976 | Vidal | 128/205.11 |
| 4,036,253 | 7/1977 | Fegan et al. | 137/ |
| 4,109,651 | 8/1978 | Steigerwald | 128/205.17 |
| 4,267,832 | 5/1981 | Hakkinen | 128/205.24 |
| 4,391,283 | 7/1983 | Sharpless et al. | 272/99 |
| 4,494,565 | 1/1985 | Sinclair et al. | 116/277 |

*Primary Examiner*—Max Hindenburg
*Assistant Examiner*—J. P. Lacyk
*Attorney, Agent, or Firm*—Dodge Bush & Moseley

[57] ABSTRACT

Apparatus for supplying oxygen or anesthetic gas through a mask (10) on the face of a patient and including a flexible gas reservoir bag (14) having a manually operated valve assembly (16) attached to an end of the bag (14) for controlling the internal fluid pressure in the bag (14). A predetermined gas supply (21) has a vent valve means (22) in its supply lines (17, 20) for diluting the predetermined gas with ambient air as desired.

6 Claims, 4 Drawing Sheets

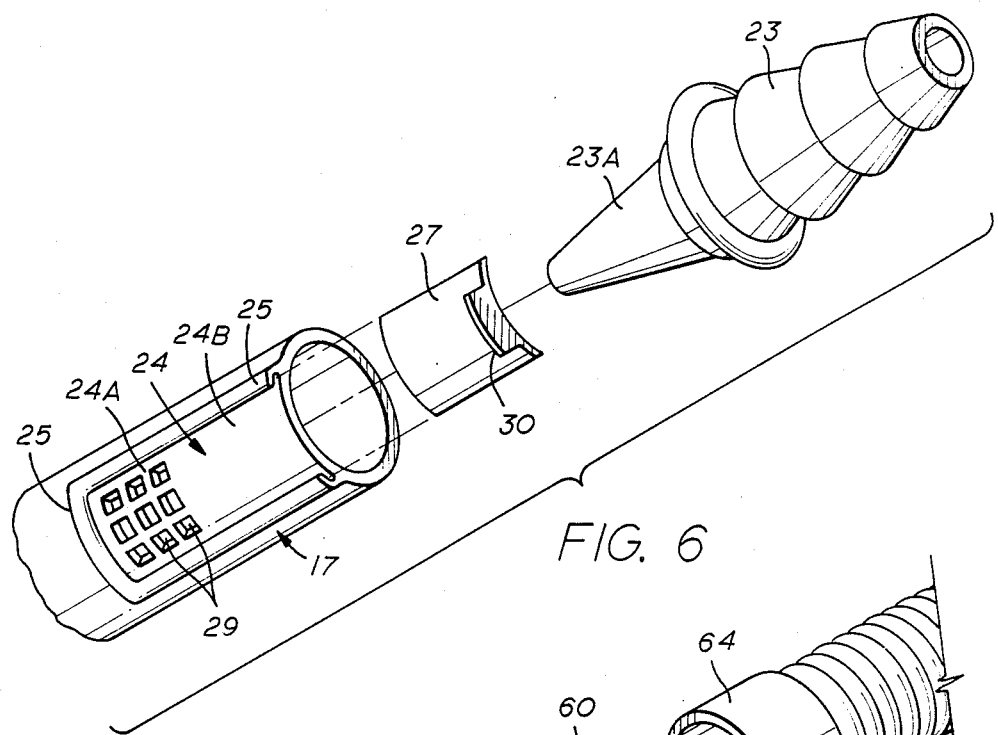
FIG. 6
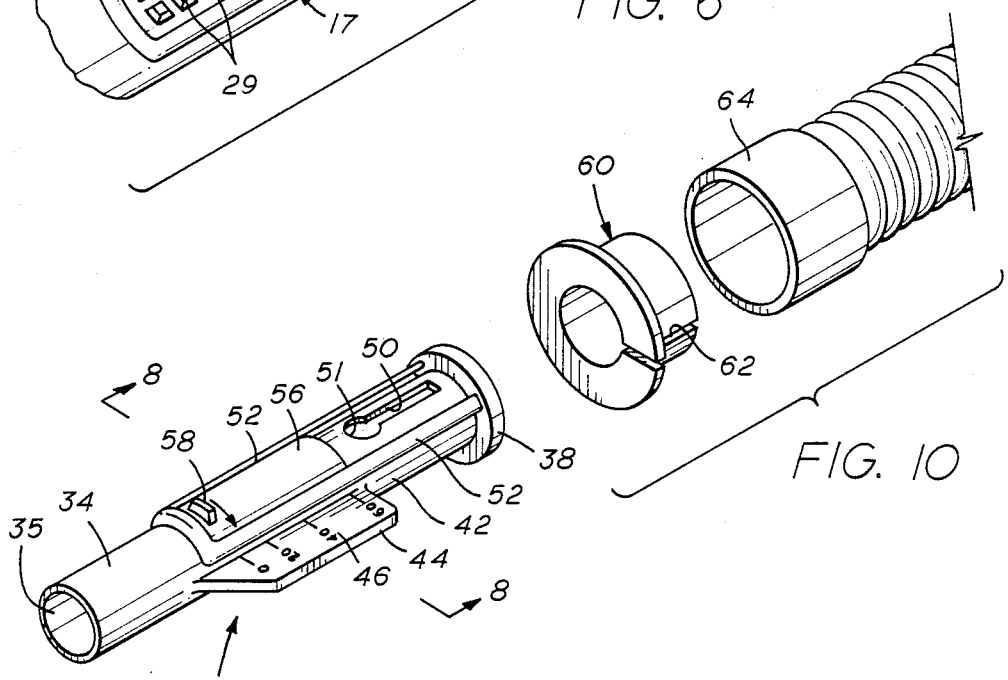
FIG. 7
FIG. 10

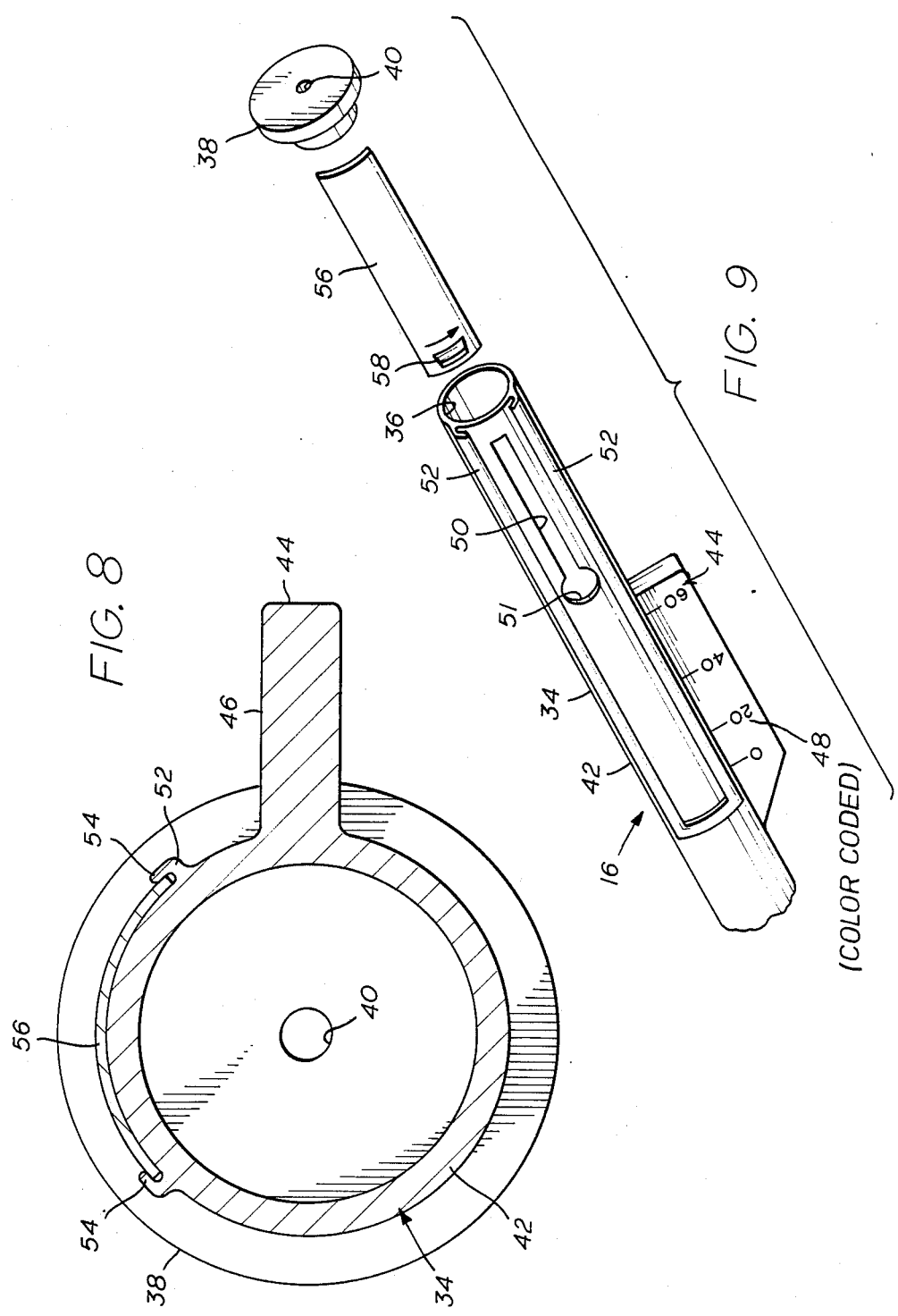

APPARATUS FOR SUPPLYING GAS TO A PATIENT

This application is a continuation of application Ser. No. 088,128, filed 8/21/87, now abandoned.

BACKGROUND OF THE INVENTION

This invention relates generally to manually operated gas delivery systems for oxygen or anesthetic gas to patients through a face mask or endotracheal tube, and more particularly to such gas delivery systems using a flexible gas reservoir bag.

Breathing quantity and quality, and therefore, related respiratory support as may be required, include three separate modes of breathing; (1) "spontaneous breathing" (normal and unassisted respiration); (2) "assisted breathing" (the addition of positive pressure during the inspiratory phase of respiration to provide an adequate volume of oxygen to the lungs); and (3) "controlled breathing" (providing both an adequate rate of breathing and an adequate inspiratory positive pressure in order to sufficiently oxygenate the lungs).

Gas supply systems for providing positive inspiratory pressure in the past generally have utilized a self-expanding semi-rigid gas reservoir bag which may be manually squeezed to supply gas through a face mask, or endotracheal tube, to the patient's lungs. Such prior devices are generally known as resuscitators and are often used by various persons in providing pre-hospital emergency medical care.

The greatest asset of such resuscitators is the ability to provide atmospheric air under positive pressure to a patient's lungs. Such resuscitators, however, are primarily of use for controlled breathing and are poorly suited for assisted breathing. These resuscitators have no applicability in situations involving spontaneous breathing.

Such resuscitators have utilized various types of valves or diaphragms for directing inspiratory ambient air, with or without various oxygen enriching devices, to a patient or for the venting of exhaled gases from a patient. Such devices presented problems including the addition of resistance to a patient's inspiratory and expiratory effort and increasing the complexity and cost of the use of the breathing systems. Because such resuscitators are often transported, size is an important consideration. In addition, because of the need for a sterile aseptic environment, such resuscitators must be sterilized after each use. Often, such devices must be dissembled for sterilization and then reassembled for reuse. Such practices increase both the cost of use and the risk of harm to a patient through a mistake in reassembly or through contamination. Such problems are aggravated by the complexity of such devices. Furthermore, the only way to provide pure oxygen with these devices is to employ a secondary bag or reservoir, receiving an oxygen supply, and which is in communication with the fluid intake means of the self-expanding bag.

Devices also exist for providing supplemental oxygen to a patient who is breathing spontaneously. Such devices, however, are not useful in situations in which the patient's condition requires assisted or controlled breathing. Additionally, these devices provide little, if any, monitoring quality of breathing as may be observed by the rhythmic expansion and contraction of a flexible reservoir bag.

While flexible gas reservoir bags have been utilized heretofore in resuscitators with various adjustable valve means at one end of the bag to control a vent thereat for varying the fluid pressure within the interior of the gas bag, such valve means have been relatively complex or difficult to operate manually with the use of any one hand of an operator. Further, such valve means have not normally included visual indicators directly adjacent the valve means for indicating the pressure being applied to a patient's lungs by a particular setting of the valve means in order to easily adapt the resuscitator for use with different types of breathing. And, while these devices function well for the spontaneously breathing patient, when oxygen is the sole gas entering the system, the absence of an oxygen dilution capability will subject the patient to the hazards and risks of breathing pure oxygen. This type of administration is especially perilous for post-operative patients an patients with pre-existing chronic obstructive pulmonary disease.

SUMMARY OF THE INVENTION

The present invention is particularly directed to non-rebreathing apparatus which functions in the absence of resistance creating inspiratory and expiratory flow directing valves. The fundamental criterion for such non-rebreathing, non-moving valve devices is the presentation at the face mask, or endotracheal tube, of a total flow of gas to sufficiently avoid accumulation of carbon dioxide. The invention herein described functions on a total flow volume which provides a safe range of applicability for administering to adults. Additionally, the total flow volume and subsequently described flexible reservoir bag and pressure values may be appropriately adjusted to accommodate the requirements of children and infants.

Briefly, the present invention is directed to apparatus for supplying gas through a mask on the face of a patient, or endotracheal tube, including a flexible gas reservoir bag connected at one end to a conduit connected to the mask and having improved valve means connected at the gas bag's other end. The improved valve means includes a manually controlled valve member, calibrated to a specific gas flow into the system, and selectively movable between predetermined positions relative to a vent to atmosphere. Suitable indicia on the valve means adjacent the movable valve member are easily visible to an operator for determining the desired position of the valve member corresponding to the desired fluid pressure of the gas to be communicated to the patient. The slidable valve member is easily adjusted by the thumb of an operator and the adjacent indicia may include color coding in addition to calibrated indicia for indicating the fluid pressure in cubic centimeters of water. For example, it is noted that (1) for spontaneous breathing, no fluid pressure would be exerted; (2) for assisted breathing a pressure of around five to forty centimeters of water would be required; and (3) for controlled breathing a pressure of around forty to sixty centimeters of water would be required. The flexible reservoir bag is utilized primarily for providing an ample supply of fresh gas and to provide positive inspiratory pressure, by squeezing the bag, when assisted or controlled breathing is required.

In addition, the present invention includes means for delivery of a separate gas, such as oxygen, to the face mask on the patient and additional valve means are provided in the separate delivery line or conduit to dilute the concentration of such separate gas by the introduction of a predetermined amount of ambient air. A slidable valve member may be easily adjusted by the thumb of an operator for this purpose and suitable indicia are provided adjacent the valve member to indicate full dilution for spontaneous breathing or no dilution for assisted or controlled breathing. When used for anesthetic gases no dilution is preferred.

Accordingly, it is an object of the invention to provide an apparatus which can be used in providing prehospital emergency medical care in situations involving spontaneous, assisted, or controlled breathing.

It is a further object of the invention to provide easily adjusted means for allowing the dilution of a predetermined gas supplied to a patient.

It is a further object of the invention to provide easily adjusted means for adjusting the venting to atmosphere of the gas contained in a flexible gas reservoir bag, thereby allowing the selection of various levels of pressure within the breathing system.

It is still a further object of the invention to provide means adjacent a movable valve member for a vent for visually indicating the corresponding gas dilution or pressure within the breathing system.

These objects, and others to become apparent in the detailed description of the invention, are accomplished by the present invention.

BRIEF DESCRIPTION OF THE DRAWINGS

FIG. 6 is an exploded view of the valve means shown on FIGS. 4 and 5;

FIG. 7 is a perspective view of the improved valve means connected to one end of the gas reservoir bag;

FIG. 8 is a section taken generally along line 8—8 of FIG. 7;

FIG. 9 is an exploded view of the valve means shown in FIGS. 7 and 8 and showing the slidable valve member adapted for actuation by the thumb of an operator; and FIG. 10 is an exploded view of an adaptor utilized when anesthetic gas is employed.

DESCRIPTION OF THE PREFERRED EMBODIMENT

Figure 1:
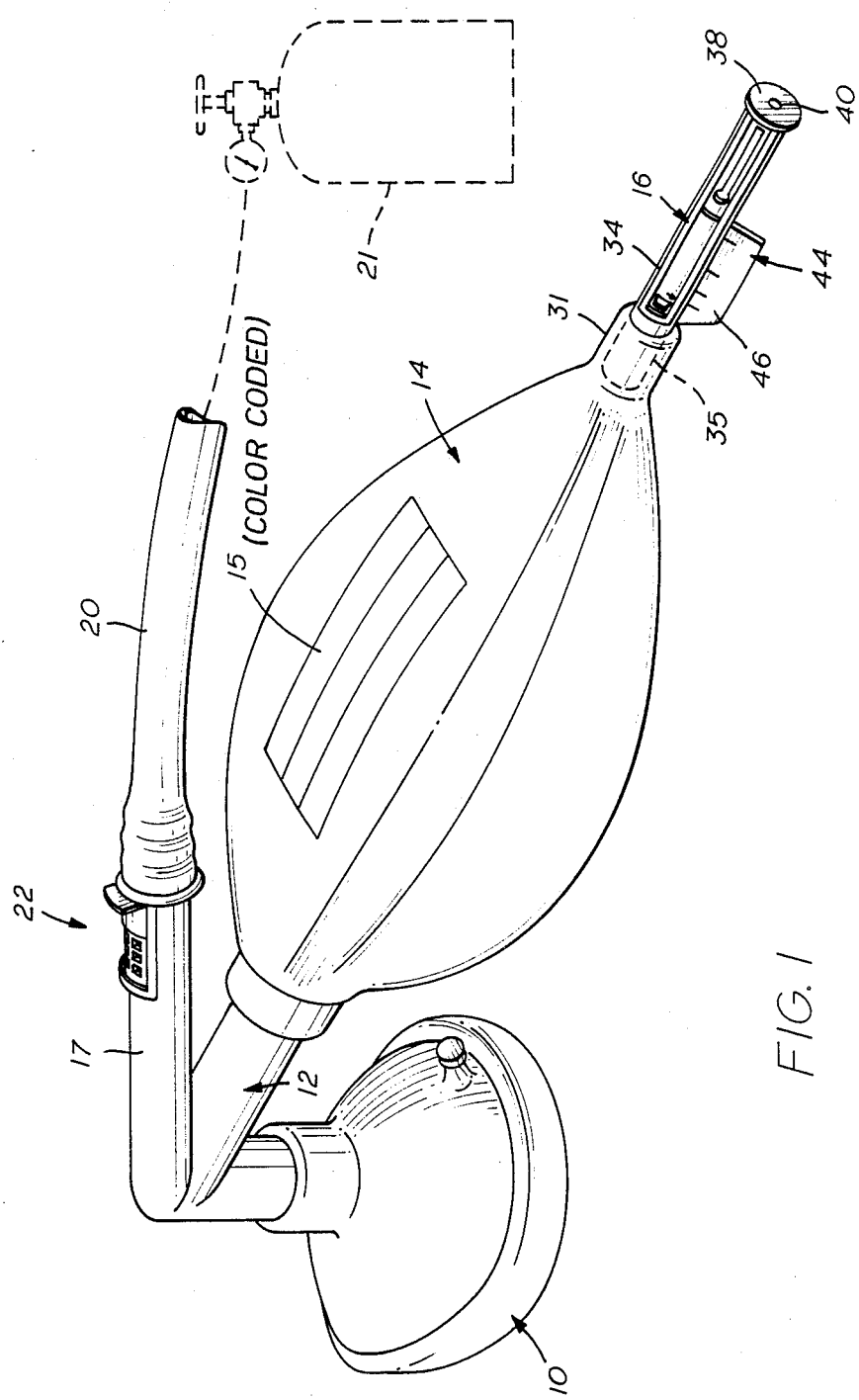
FIG. 1 is a perspective view of the apparatus comprising the present invention including a face mask, a flexible gas reservoir bag having improved valve means connected thereto, and a separate gas delivery conduit having improved valve means thereon for diluting a predetermined gas supplied to the patient.

Referring now particularly to FIG. 1, an apparatus is illustrated for a manually operated gas supply system to a patient in accordance with the present invention. A mask 10 is normally fitted over the face of a patient and allows a patient to inhale and exhale through mask 10. In some instances, it may be desirable or necessary to supply gas to a patient through an endotracheal tube (not shown) as is well known.

Connected to mask 10 and in fluid communication therewith is a main gas conduit 12 forming an elbow. One end of main conduit 12 is connected to mask 10 and the other end of main conduit 12 is connected to a flexible gas reservoir bag generally indicated 14 containing a gas mixture from inhaled and exhaled gases of the patient for indicating by contraction and expansion the breathing quality of the patient. Bag 14 may be provided with indicia 15 therein as indicated on the table set forth hereinafter. Connected to the other end of gas bag 14 and allowing fluid communication between the interior of gas bag 14 and atmosphere is an improved valve means or valve assembly generally indicated 16 and forming an important part of this invention.

Also connected to main gas conduit 12 and in fluid communication therewith is a branch gas supply conduit 17 having a flexible gas supply tube 20 attached thereto and leading to a metered gas supply means 21. Gas supply means 21 provides a predetermined gas, such as oxygen or an anesthetic, to face mask 10 and the patient through gas supply tube 20, branch conduit 17, and main conduit 12. Located on branch conduit 17 is an improved valve means or valve assembly generally indicated 22 for allowing the introduction of air into branch conduit 17 from a vent to atmosphere for diluting the gas being supplied from gas supply means 21.

Figure 2:
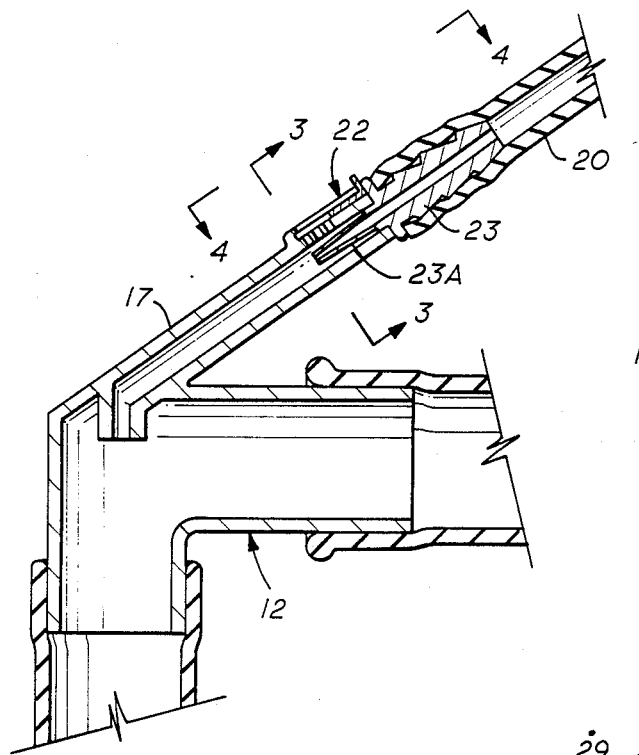
FIG. 2 is an enlarged longitudinal sectional view of the main conduit from the flexible bag and the branch conduit from the separate gas delivery conduit adjacent the face mask and showing the valve means on the branch conduit for diluting the supply of the separate gas.
Figure 3:
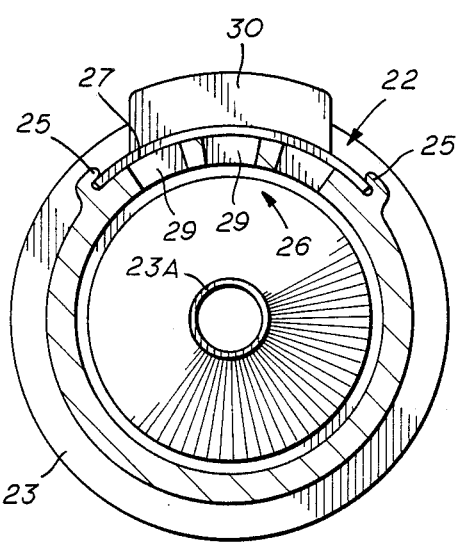
FIG. 3 is a sectional view taken generally along line 3—3 of FIG. 2 and showing the improved dilution valve assembly.

Referring now particularly to FIG. 2 in which conduits 12 and 17 are shown in section, branch conduit 17 includes a flanged end nipple 23 which receives an end of flexible supply tube 20 and a constriction nozzle 23A forming a small diameter orifice adjacent valve means 22 and end nipple 23. Valve means 22, particularly as shown in FIGS. 3-6, includes an outer base surface 24 on branch conduit 17 defined by flanging 25 extending outwardly from conduit 17 and receiving a slidable plate member or cover 27 for sliding movement along base surface 24. Base surface 24 is divided into two longitudinally extending areas 24A and 24B along branch conduit 17 as shown particularly in FIG. 6. Base surface area 24A has a plurality of vent openings 29 arranged in spaced rows thereon which extend to atmosphere through branch conduit 17 and are of a sufficiently small size to minimize the entrance of foreign matter. Vent openings 29 are adapted to be opened or closed by adjustment of plate member 27 along base surface 24 by manual engagement of a tab 30 extending from plate member 27. If desired, base surface 24A having openings 29 therein may be colored green to indicate when exposed by cover 27 that diluting ambient air is being entrained through openings 29 in the gas delivery system for spontaneous breathing. Base surface 24B which has a solid surface may be colored yellow and red to indicate when exposed by cover 27 that openings 29 are closed for blocking diluting ambient air during assisted or controlled breathing.

Although the present invention is applicable for supplying gases other than oxygen to a patient, such as providing a patient with an anesthetic, the primary use of the present invention is in situations in which it is desirable to provide supplemental oxygen to a patient. For situations involving either assisted or controlled breathing, supplying a patient with pure oxygen is appropriate. In situations involving spontaneous breathing, however, it is inadvisable to provide a patient with pure oxygen. Consequently, the present invention incorporates the improved valve means 22 for allowing the dilution of oxygen being supplied to a patient.

As the oxygen from gas supply means 21 flows into branch conduit 17, the oxygen passes through constriction nozzle 23A, which defines an orifice having a diameter of generally one-fourth (¼) the diameter of the bore opening formed by nipple 23 receiving oxygen from gas supply tube 20. Constriction nozzle 23A acts as a venturi to increase the velocity of fluid flow thereat adjacent valve assembly 22 and to assist the inflow of air through valve assembly 22. Thus, upon opening of the vent openings 29 to atmosphere by manual adjustment of slidable plate member 27, the pressure of the oxygen supplied through branch conduit 17 is decreased.

When plate member 27 is moved to a predetermined position leaving vent openings 29 open to atmosphere, the flow of oxygen or some other predetermined gas in branch conduit 17 past open vent openings 29 causes air to be entrained through vent openings 29 into the interior of branch conduit 17 with the resultant gas mixture then flowing into main conduit 12. By selectively positioning slidable plate member 27 relative to vent openings 29, either fully exposing all vent openings or fully covering all vent openings, the entrainment of air can be controlled. Vent openings 29 are of such a size so that when fully open, the entraining effect draws in a volume of air through vent openings 29 which is approximately equal to the volume of oxygen supplied through gas supply tube 20. The oxygen is supplied to the patient through gas supply tube 20 from gas supply means 21 of a type well known in the art, such as a standard oxygen tank system with a metering capability of fifteen (15) liters per minute (LPM) of gas.

Figure 4:
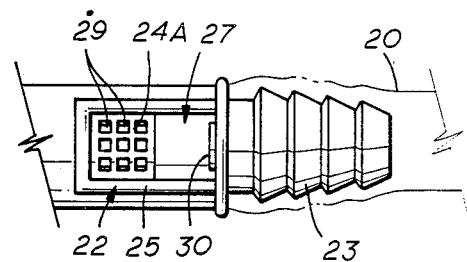
FIG. 4 is an enlarged top plan of the valve means on said branch conduit looking generally along line 4—4 of FIG. 2 and showing the valve means in a fully open position providing a vent to atmosphere.
Figure 5:
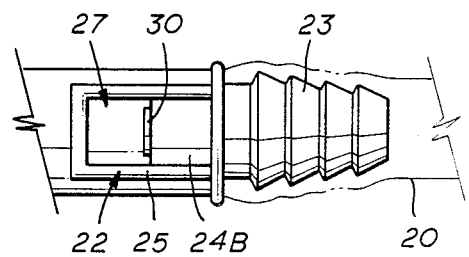
FIG. 5 is an enlarged top plan similar to FIG. 4 but showing the valve means in a fully closed position blocking the vent to atmosphere.

Referring to FIG. 4, slidable plate member 27 is positioned over surface area 24B to leave vent openings 29 fully open to atmosphere. FIG. 5, which is generally similar to FIG. 4, shows slidable plate member 27 over surface area 24A in a position fully blocking vent openings 29. In this position, vent openings 29 are closed and no air is entrained into branch conduit 17, thereby allowing a supply of pure oxygen to the patient.

FIG. 6 shows slidable cover or plate member 27 removed from the pocket formed by flanging 25 and also shows the adjacent nozzle 23A removed from branch conduit 17. An extending tab 30 on plate member 27 is adapted to be manually engaged by a thumb (or other digit) of an operator with minimal difficulty for easily adjusting the position of plate member 27 relative to vent openings 29.

Referring now to FIGS. 7-9, improved valve means 16 for flexible gas reservoir bag 14 is illustrated. Valve means 16 comprises an elongated tubular body 34 having one end 35 open and fitting within a tubular end extension 31 of bag 14. The opposite distal end 36 of tubular body 34 has a flanged end plug 38 secured therein having a small diameter end port 40 which acts as a safety pressure relief to limit the build-up or increase in static pressure within bag 14 in the event the patient or gas delivery system is unattended temporarily. Tubular body 34 is preferably formed of a molded plastic material and has intermediate body portion 42 which includes an outwardly extending flange generally indicated 44. Flange 44 has a planar surface 46 which provides a visible surface area for desired indicia 48 thereon which is easily visible to an operator. Indicia 48 may include color coding and a graduated scale of desired measurements, such as measurements for centimeters of water to indicate the interior pressure of gas bag 14, for example.

Provided in tubular body 34 adjacent end 36 is an elongate slot 50 having an enlarged end portion 51 and providing a vent to atmosphere. Extending about vent or slot 50 is flanging 52 projecting outwardly from the outer surface of tubular body 34 and extending to end 36. Flanging 52 has inturned lips 54 thereon which receive a sliding arcuate plate member 56 for sliding movement relative to vent 50. A tab 58 extending from plate member 56 is adapted to be engaged by the thumb of an operator for adjustment of plate member 56 and associated vent 50. If vent 50 is fully closed and vent openings 29 are fully closed, a build-up or increase in the static pressure within reservoir bag 14 may occur, but pressure relief port 40 remains open and is sized to limit the static pressure within reservoir bag 14 to around thirty (30) cubic centimeters of water in the event the gas delivery system is unattended temporarily.

In the event the present gas delivery system is utilized for anesthetic gas, FIG. 10 shows a scavenging device including a tubular adapter generally indicated at 60 and slotted at 62 to permit positioning of adapter 60 about tubular body 34 over vent 50. Then, suitable tubing shown at 64, such as corrugated anesthetic tubing, is connected to adapter 60 and diverts the anesthetic gas to a suitable storage container. Suitable taping may be utilized to seal tubing 64.

Referring now to FIGS. 1 and 7, indicia 48 on flange 44 of valve assembly 16 shows the internal pressure of gas bag 14 in centimeters of water on FIG. 7, and indicia 15 on gas reservoir bag 14 in FIG. 1 has a table as illustrated below. The various indicia are selected to allow an operator to visually perceive what adjustments need to be made in order for the system to effectively respond to the patient's condition. The following table positioned at 15 on bag 14 illustrates the use of color as indicating means and how it corresponds to the adjustments needed in various patient conditions:

| Patient Condition | Oxygen Flow from Gas Supply 21 | Status of Vent 29 (Valve 22) | Oxygen Content to Patient | Status of Vent 52 (Valve 16) | Interior Pressure of Gas Bag 14 (Centimeters of Water) |
|---|---|---|---|---|---|
| Spontaneous Breathing (Green Color) | 7 LPM | Open | 60% | Fully Open | 0 |
| Assisted Breathing (Yellow Color) | 14 LPM | Closed | 100% | Partially Closed | Generally between 20 and 40 |
| Controlled Breathing (Red Color) | 14 LPM | Closed | 100% | Partially to Fully Closed | Generally between 40 and 60 |

It is noted that atmospheric air contains twenty (20) percent oxygen and eighty (80) percent nitrogen. Exhaled gases include thirteen (13) percent oxygen, five (5) percent carbon dioxide, seventy-five (75) percent nitrogen and six (6) percent water. For spontaneous breathing (normal and unassisted breathing) sixty (60) percent oxygen and forty (40) percent nitrogen are supplied. A desired oxygen supply is provided a patient by the present invention including valve assembly 16 for reservoir bag 14 which provides a fluid pressure control means with associated indicia thereon, and valve assembly 22 which provides an oxygen dilution with associated indicia thereon. Valve assemblies 16 and 22 are not movable in response to suction and pressure resulting from inhalation and expiration of the patient but are manually set and controlled by an operator.

In operation for oxygen administration for spontaneous breathing, valve assemblies 16 and 22 are fully open and oxygen is supplied from oxygen tank 21 at a rate of around seven (7) liters per minute (LPM) as indicated by the green color on the indicia of valve assemblies 16 and 22. Valve assembly 22 when fully open supplies ambient air at a rate of around seven (7) LPM for a total flow of around fourteen (14) LPM with an oxygen concentration of sixty (60) percent. The gas mixture is communicated to bag 14 and valve assembly 16 which is fully open. The sizing of vent openings 29 and vent openings 50 are established in order to provide when fully open a static pressure within the entire system of less than around one (1) centimeter of water pressure which presents a minimal resistance to breathing in the spontaneous breathing mode. The sizing of the vent openings 29 and 50 is also established to satisfy the requirement for assisted and controlled breathing as set forth below.

In operation for oxygen administration for assisted or controlled breathing, oxygen from oxygen tank 21 may be delivered at a rate of fourteen (14) liters per minute (LPM), for example. With valve assembly 22 closed, around fourteen (14) LPM of one hundred (100) percent oxygen flows into main conduit 12, reservoir 14, and valve assembly 16. With an input of fourteen (14) LPM of oxygen, valve assembly 16 may be adjusted to provide a range of pressure generally between twenty (20) and sixty (60) centimeters of water pressure as measured at mask 10 upon a single manual squeezing of reservoir bag 14. Thus, manual adjustments of valve assemblies 16 and 22 may be made to provide the desired fluid pressure. Normally a range of pressure from twenty (20) to forty (40) centimeters of water as measured at the face mask upon a single manual squeezing of bag 14 would be provided for assisted breathing as indicated by the yellow color on the indicia of valves 16 and 22, and a range between forty (40) and sixty (60) centimeters of water would be provided for controlled breathing as indicated by a red color on the indicia of valves 16 and 22. Pressure relief port 40 is of a size to limit a static pressure increase to around a maximum pressure of around thirty (30) centimeters of water with valve assemblies 16 and 22 being closed and as measured at mask 10.

In operation for the administration of anesthetic gas, a predetermined volume of an anesthetic gas mixture from a suitable source is supplied with valve assembly 22 in a closed position and valve assembly 16 under the control of an anesthesiologist. Adapter 60 and tubing 64 are also positioned about valve assembly 16.

While only a preferred embodiment of the invention has been illustrated and described herein, it is apparent that alterations, changes, and modifications may be made to the invention as described herein without departing from the scope and spirit thereof.

What is claimed is:

1. Apparatus for administering a predetermined gas to a patient comprising:

a main gas conduit adapted to be connected to a face mask;

a flexible gas reservoir bag having one end connected to said main gas conduit and adapted to be manually squeezed for supplying gas to said patient;

first valve means connected to the other end of said gas reservoir bag and in fluid communication with the interior of said gas reservoir bag, said valve means including a vent to atmosphere and a valve member selectively movable between predetermined positions relative to said vent for controlling the flow of gas through said vent;

means adjacent said first valve means to permit upon squeezing of said reservoir bag an indication of the internal fluid pressure of said reservoir bag corresponding to said positions of said valve member relative to said vent;

a branch gas supply conduit having one end connected to said main gas conduit and adapted to supply a predetermined gas to said main gas conduit;

second valve means associated with said branch conduit for permitting the introduction of air into said branch conduit to dilute said predetermined gas, said second valve means including a vent to atmosphere and a slidable valve member over said vent selectively movable longitudinally of said branch conduit relative to and adjacent said vent; and means adjacent said second valve member for indicating the position of said valve member over said vent and the relative dilution of said predetermined gas corresponding to said positions of said valve member.

2. Apparatus for administering a predetermined gas to a patient comprising:

a main gas conduit adapted to be connected to a face mask;

an elongate flexible gas reservoir bag having one end connected to said main gas conduit and adapted to be manually squeezed for supplying gas to said mask;

first valve means connected to the other end of said gas reservoir bag and in fluid communication with the interior of said gas reservoir bag, said first valve means including an elongate tubular body having an elongate vent opening therein extending longitudinally of said body, a plate valve member selectively movable longitudinally of said body between predetermined positions relative to said vent opening for controlling the flow of gas through said vent opening, and indicia including color coding on said elongate tubular body adjacent said movable valve member and said vent opening to indicate the positions of said movable valve member relative to said vent opening;

a branch gas supply conduit having one end connected to said main gas conduit and adapted to supply a predetermined gas to said main gas conduit;

second valve means associated with said branch conduit for permitting the introduction of air into said branch conduit to dilute said predetermined gas, said second valve means including a vent to atmosphere and a valve member selectively movable relative to and adjacent said vent;

a venturi nozzle within said branch conduit adjacent said vent to assist the entraining of air upon opening of said vent;

indicia on said flexible bag including a table and color coding to indicate adjustments needed in said first and second valve means for various patient conditions; and means on said branch conduit adjacent said second valve means for indicating the relative dilution of said predetermined gas corresponding to said positions of said valve member.

3. In apparatus having a main conduit connected to a gas reservoir bag at one end and to a mask to be fitted over a patient's face at the other end, and a branch conduit of a circular cross-section leading from said main conduit to a predetermined gas supply means; improved valve means in said branch conduit to permit the introduction of air into said branch conduit for diluting the predetermined gas therein comprising:

a plurality of vent openings spaced longitudinally of said branch conduit;

a manually slidable plate member of an arcuate cross section fitting against the outer surface of said branch conduit and selectively movable along the longitudinal axis of said branch conduit between predetermined positions relative to said vent openings for covering and uncovering said vent openings;

means on said branch conduit mounting said plate member adjacent said vent openings for sliding adjustable movement relative to said vent openings;

means on said branch conduit adjacent the plate member for indicating the position thereof for permitting gas to be introduced into said branch conduit to dilute said predetermined gas; and a venturi nozzle within said branch conduit adjacent said vent openings to assist the entraining of air upon opening of said vent openings.

4. In apparatus for administering gas to a patient having a main conduit connected to an elongate gas reservoir bag at one end and to a mask to be fitted over the patient's face at the other end, and a branch conduit leading from said main conduit to a predetermined gas supply means; improved valve means for venting the gas in said gas reservoir bag comprising:

an elongated tubular member of a generally circular cross-section having an end adapted to be connected in fluid communication with one end of said flexible gas reservoir bag and having an elongate vent extending longitudinally thereof;

a plate member mounted on said tubular member over said vent for movement in a longitudinal direction along said tubular member between predetermined positions relative to said vent;

means on said elongated tubular member mounting said plate member for sliding adjustable movement between said predetermined positions for controlling the size of said vent exposed to atmosphere;

means on said plate member engageable manually for movement of said plate member in said longitudinal direction;

a flange extending laterally outwardly from said tubular member and having a generally planar surface adjacent said slidable plate member; and graduated means on said planar surface adjacent said slidable plate member to permit upon squeezing of said bag an indication of the internal fluid pressure thereof corresponding to said positions of said slidable plate member relative to said vent.

5. In apparatus according to claim 4 wherein said valve means has a small pressure relief port for limiting the increase in static pressure within said flexible bag upon non-use of the gas administering system.

6. In apparatus for administering gas to a patient having a main conduit connected to an elongate gas reservoir bag at one end and to a mask to be fitted over the patient's face at the other end, and a branch conduit leading from said main conduit to a predetermined gas supply means; improved valve means for venting the gas in said gas reservoir bag comprising:

an elongated tubular member having an end adapted to be connected in fluid communication with one end of said flexible gas reservoir bag and having a vent extending longitudinally thereof;

a flow control member mounted on said tubular member over said vent for movement in a longitudinal direction along said tubular member between predetermined positions relative to said vent;

means on said elongated tubular member mounting said flow control member for sliding adjustable movement between said predetermined positions for controlling the size of said vent exposed to atmosphere;

means on said flow control member engageable manually for movement of said flow control member in said longitudinal direction;

a flange extending laterally outwardly from said tubular member and having a generally planar surface adjacent said flow control member;

graduated means on said planar surface adjacent said flow control member to permit upon squeezing of said bag an indication of the internal fluid pressure thereof corresponding to said positions of said flow control member relative to said vent;

an anesthetic adapter for selective fitting on said tubular member over said vent and for receiving anesthetic gas flow from said reservoir bag; and suitable tubing connected to said adapter to receive anesthetic gas therefrom for flow to a suitable storage container.

* * * * *